(12) United States Patent
Bolleter

(10) Patent No.: US 8,992,221 B2
(45) Date of Patent: Mar. 31, 2015

(54) DENTURE SYSTEM

(75) Inventor: Philip Bolleter, Zurich (CH)

(73) Assignee: DentalPoint AG, Zurich (CH)

( * ) Notice: Subject to any disclaimer, the term of this patent is extended or adjusted under 35 U.S.C. 154(b) by 131 days.

(21) Appl. No.: 13/981,596

(22) PCT Filed: Jan. 24, 2012

(86) PCT No.: PCT/EP2012/051069
§ 371 (c)(1),
(2), (4) Date: Jul. 24, 2013

(87) PCT Pub. No.: WO2012/101135
PCT Pub. Date: Aug. 2, 2012

(65) Prior Publication Data
US 2013/0309630 A1    Nov. 21, 2013

(30) Foreign Application Priority Data

Jan. 25, 2011 (CH) .......................... 118/11

(51) Int. Cl.
*A61C 8/00* (2006.01)
*A61C 8/02* (2006.01)

(52) U.S. Cl.
CPC ............... *A61C 8/0066* (2013.01); *A61C 8/005* (2013.01); *A61C 8/0001* (2013.01); *A61C 8/0006* (2013.01); *A61C 8/0077* (2013.01); *A61C 8/008* (2013.01)
USPC ....................................................... 433/173

(58) Field of Classification Search
CPC ..... A61C 8/006; A61C 8/0054; A61C 8/0057
USPC ...................................... 433/173–176, 201.1
See application file for complete search history.

(56) References Cited

U.S. PATENT DOCUMENTS

| 4,657,510 | A | * | 4/1987 | Gittleman | 433/173 |
|---|---|---|---|---|---|
| 5,092,771 | A |   | 3/1992 | Tatum, III | |
| 5,197,881 | A | * | 3/1993 | Chalifoux | 433/173 |
| 5,695,335 | A | * | 12/1997 | Haas et al. | 433/173 |
| 5,782,918 | A | * | 7/1998 | Klardie et al. | 606/60 |

(Continued)

FOREIGN PATENT DOCUMENTS

| EP | 2 143 398 A1 | 1/2010 |
|---|---|---|
| WO | 00/54696 A1 | 9/2000 |

*Primary Examiner* — Cris L Rodriguez
*Assistant Examiner* — Hao D Mai
(74) *Attorney, Agent, or Firm* — Janet Sleath; Speckman Law Group PLLC

(57) ABSTRACT

The invention relates to a denture system comprising an implant (1) for osseointegration into a jawbone and comprising an abutment (2) with an insertion stem (6) that can be inserted into a receiving opening (4) of the implant (1). At least one shoulder (9) is formed on the insertion stem (6), said shoulder running at least partly in a radial manner with respect to a longitudinal axis of the insertion stem. At least one stop (5) is provided on an inner circumferential surface of the receiving opening (4), said stop running at least partly in a radial manner. In a first rotational position between the insertion stem (6) and the implant (1), the abutment (2) can be moved relative to the implant (1) in an axial direction, and in a second rotational position in which the insertion stem (6) is rotated about the longitudinal axis relative to the implant (1) by an angle with respect to the first rotational position, at least one shoulder (9) axially engages behind a stop (5) such that a movement between the implant (1) and the abutment (2) in an opposite axial direction is blocked.

14 Claims, 2 Drawing Sheets

(56) References Cited

U.S. PATENT DOCUMENTS

| | | | |
|---|---|---|---|
| 5,823,776 A * | 10/1998 | Duerr et al. | 433/173 |
| 5,908,298 A * | 6/1999 | Durr et al. | 433/173 |
| 6,116,904 A * | 9/2000 | Kirsch et al. | 433/173 |
| D441,448 S * | 5/2001 | Kumar | D24/156 |
| 6,315,563 B1 * | 11/2001 | Sager | 433/173 |
| 6,382,977 B1 * | 5/2002 | Kumar | 433/214 |
| 6,517,543 B1 * | 2/2003 | Berrevoets et al. | 606/304 |
| 6,733,291 B1 * | 5/2004 | Hurson | 433/173 |
| 7,338,286 B2 * | 3/2008 | Porter et al. | 433/173 |
| 7,726,969 B2 * | 6/2010 | Walther | 433/174 |
| 8,033,826 B2 * | 10/2011 | Towse et al. | 433/172 |
| 8,070,491 B2 * | 12/2011 | Mundwiler et al. | 433/163 |

* cited by examiner

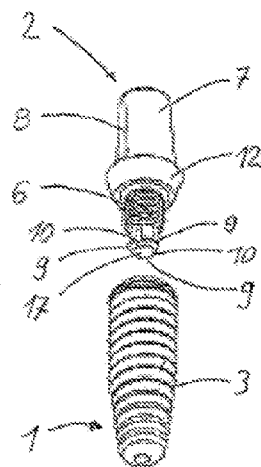
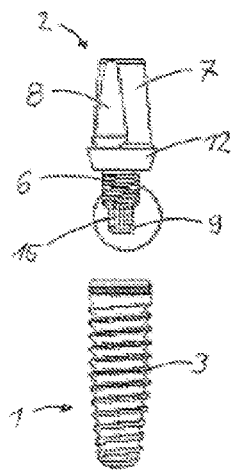
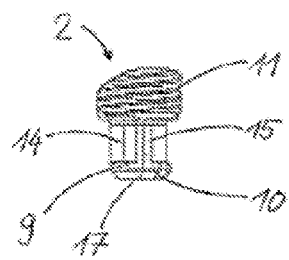
Fig. 1    Fig. 2a    Fig. 2b
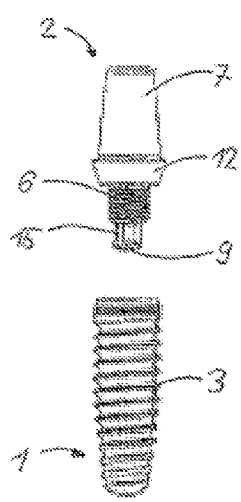
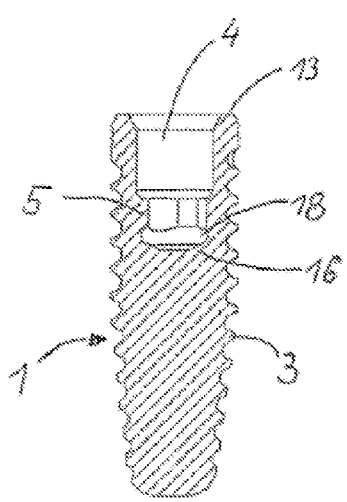
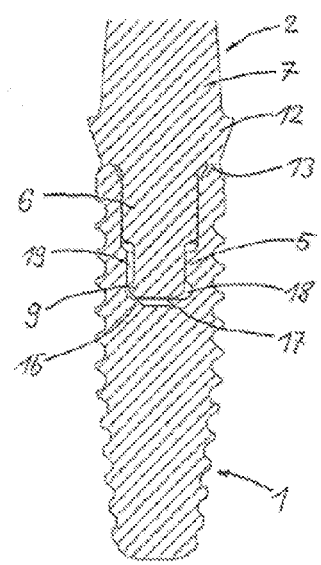
Fig. 2c    Fig. 3    Fig. 4

DENTURE SYSTEM

This application is the US national phase entry of International Patent Application no. PCT/EP2012/051069, filed Jan. 24, 2012, which claims priority to Swiss patent application no. 0118/11, filed Jan. 25, 2011.

FIELD OF THE INVENTION

The present invention relates to a denture system comprising an implant for osseointegration into a jawbone, and comprising an abutment to be inserted into the implant.

BACKGROUND OF THE INVENTION

Known by the terms tooth implant or dental implant, a wide variety of denture systems have been available on the market for years and have in some cases been used with great success. The terms tooth implant or dental implant generally denote the denture per se and should not be confused with the actual implant body which, as a replacement for a tooth root, is correctly designated as the implant. In the text below, the terms tooth implant and implant body or implant are clearly distinguished, where the tooth implant designates the denture, which comprises the implant body for anchoring in the jawbone. Two-part and three-part tooth implants are mainly available on the market, of which the three-part implants for replacement of an individual tooth generally consist of an endosteal implant or implant body, an abutment (also called a connection part or implant post), and a crown, a bridge or another prosthetic.

The abutment allows the dentist to orient the crown with respect to the implant, such that the exact position of the crown in the dental arch is not dependent only on the position of the implant body. For this purpose, the abutment has to be positioned in the implant according to a predefined orientation, after the implant has been anchored in the jaw.

Customary implant forms include blade, needle, screw, cylinder and cone implants, which are each used for different indications. In principle, subperiosteal and endosteal implants can be used. Commonly used endosteal implants are substantially cylindrical and are screwed or hammered into a drilled hole in the jawbone or directly into the jawbone. At the coronal end, the implants are provided with an open blind bore for receiving the abutment. In the last few decades, the material mainly used has been titanium, since it has a modulus of elasticity similar to the jawbone and has excellent biocompatibility. Alternatively, ceramics can be used, e.g. zirconia ceramic. In such tooth implants, the crown, mostly made of conventional dental ceramic and/or metal, is adhesively bonded or cemented onto the abutment or the one-part implant/abutment construction or secured thereon by mechanical means.

EP 0 879 024 B1 discloses a system in which a solid conical abutment is screwed into an implant. A receiving opening of the implant is likewise correspondingly formed with a conical shape. A conical shape of this kind is favored by dentists since it simplifies the implantation, in particular also the taking of impressions and the production of master models. The conical implant-abutment connection places high demands on the precision fit of the components, since it is both a form-fit and also a force-fit connection. Since the dental implants have to take up considerable alternating loads during chewing, even the very slightest mobility between the screwed components leads to abrasion and wear. Moreover, the screwing-together of abutment and implant is a complicated procedure in which the threads first of all have to engage in each other and then the abutment, generally by being rotated several times, is introduced axially into the implant.

WO 2006/084346 A1 discloses an implant system with an abutment made of a non-metallic material, which system comprises an implant and a prosthesis support, which in turn comprises an abutment and a collar element. Essential features of the implant system are that the parts of the implant system are pushed linearly into one another and adhesively bonded to one another. Between a substantially cylindrical base post and a head part, the abutment has a cylindrical neck part with a lower projection, which is designed as a polygon and serves for the radial positioning of the abutment in a corresponding recess in the shoulder of the implant. The central bore in the implant for receiving the base post is provided with an inner thread, which allows a screw cap or a spacer to be screwed in during the process of incorporation. After the incorporation, a collar element is pushed over the neck area of the abutment, and the base post is adhesively bonded into the threaded bore of the implant. A central and continuous axial channel is provided in the abutment to allow the adhesive to flow off A disadvantage of this system lies in the considerable technical effort in producing the central axial channel in the abutment and in the mechanical loads and stresses to which the abutment is exposed.

EP 1 728 486 A1 discloses an implant system with an implant and an abutment, in which the abutment is provided with means for blocking the abutment in rotation in the implant. A receiving opening in the implant is designed in such a way that a base portion of the abutment can be inserted substantially with a form fit into the receiving opening at the desired angle position and is secured in this position by a separate screw on the implant.

In the known systems in which an abutment is pushed into an implant, the abutment has to be held in position by application of a force while, for example, an integral bond is formed by the adhesive material. As a result of the pressing force, adhesive is distributed along the superposed surfaces, can partially swell out of the interstices and, during hardening, can change the position between abutment and implant, e.g. by lifting the abutment in the implant (pump effect). This causes difficulties, particularly in the case of bone-level implants. When inserting the abutment, the person providing the treatment is often under pressure of time, since the adhesive material often hardens quickly. The person providing the treatment scarcely has time to check the correct position of the abutment relative to the implant, and there is a risk of incorrect positioning. For a patient, the time waiting for the abutment to be secured is unpleasant, since constant pressure applied to the jawbone has to be withstood.

SUMMARY

The object of the invention is to make available a denture system that reduces the abovementioned disadvantages. The object is also to create a denture system that has good mechanical stability, minimizes the risk of cracks or incorrect positioning, can be fitted in place in a simple and exact manner, reduces the inconvenience to the patient, and has a cost-effective design.

According to the invention, this object is achieved by a denture system comprising an implant for osseointegration into a jawbone, and an abutment with an intersection stem that can be inserted into a receiving opening of the implant, wherein at least one shoulder is formed on the insertion stem, said shoulder extending at least in part radially with respect to a longitudinal axis of the intersection stem and at least one stop is provided on an inner circumferential surface of the receiving opening, said stop extending at least in part radially, wherein in a first rotation position between insertion stem and implant, the abutment is movable relative to the implant in an axial direction, and, in second rotation position, in which the insertion stem is rotated about the longitudinal axis relative to the implant by an angle with respect to the first rotation position, at least one shoulder engages axially behind a stop in such a wax that the abutment is fixed in the axial direction in the implant. Advantageous designs and further illustrative embodiments are described below.

A denture system according to the present invention comprises an implant for osseointegration into a jawbone, and an abutment with an insertion stem that can be inserted into a receiving opening of the implant. At least one shoulder is formed on the insertion stem, said shoulder extending at least in part radially with respect to a longitudinal axis of the insertion stem or of the receiving opening, which shoulder can serve as a locking shoulder. At least one stop is provided on an inner circumferential surface of the receiving opening, said stop extending at least in part radially. In a first rotation position between insertion stem and implant, namely the insertion rotation position, the abutment is movable relative to the implant in an axial direction, preferably movable exclusively in an axial direction. In this position, shoulders and stops are arranged offset in the circumferential direction and can be guided past one another in the axial direction. The abutment is inserted into the receiving opening and, in the insertion rotation position, is introduced axially into the receiving opening until it is in a starting position, in which a shoulder is arranged, in an axial insertion direction, behind a stop. From the starting position, the abutment can be rotated to a second rotation position, namely the engaged rotation position or locked rotation position. The insertion stem is rotated about the longitudinal axis relative to the implant by an angle with respect to the first rotation position, until at least one shoulder engages axially behind a stop, in such a way that the abutment is fixed in the axial direction in the implant. This means that a movement in an opposite axial direction, counter to the direction of insertion, between implant and abutment is blocked. A stop in the receiving opening of the implant can thus serve as a blocking stop, on which a shoulder of the insertion stem abuts in the engaged rotation position, as a result of which the abutment is blocked against being pulled out or pushed out of the implant. Therefore, in the second rotation position, the at least one stop in the implant can produce, together with the at least one shoulder of the abutment, a form-fit axial lock between implant and abutment.

In a denture system according to the present invention, shoulders and stops are positioned in such a way that, after it has been rotated to the locked rotation position, the abutment adopts a desired setting relative to the implant. In order to secure the abutment in the implant, an adhesive can be used in a known way, for example. With the aid of the axial lock, the abutment remains in the desired axial setting in the implant, without pressure having to be exerted axially on the abutment. Despite resistance caused by the adhesive or caused by the adhesive being pressed out laterally, the abutment remains axially fixed without application of force and can be secured in the desired position by hardening of the adhesive.

A shoulder of the insertion stem extends substantially in the circumferential direction around the insertion stem. An engagement surface of a shoulder, on which surface a stop of the implant engages, preferably extends in a plane perpendicular to the longitudinal axis of the insertion stem. However, the engagement surface can also be slightly inclined with respect to this plane, or to a circumference line, i.e. for example along a helical line about the longitudinal axis. In the circumferential direction, a shoulder has at least one interruption or recess in at least one circumferential area. The interruption is at least so large that a stop of the implant can be guided axially through. Preferably, several shoulders are formed along the circumferential direction of the insertion stem and protrude substantially radially from the insertion stem in different directions. Interruptions are provided between each of the individual shoulders. Preferably, as many stops are provided in the receiving opening as there are shoulders on the abutment. A plurality of shoulders permits secure locking and positioning of the abutment in the implant. Moreover, contact forces between shoulders and stops can be distributed across several contact surfaces.

Several shoulders can be arranged about the circumference symmetrically with respect to the longitudinal axis. For example, two or four shoulders can be arranged in mirror symmetry. In the case of three or five shoulders, these can be oriented point-symmetrically. Of course, it is also possible to provide more than five shoulders. The shoulders of the abutment can be designed, for example, as an N-edge shoulder on the insertion stem, where N is the number of shoulders. The individual shoulders protrude, for example, in the form of ribs with axial edges, between which the interruptions extend. The stops in the implant are arranged according to the position of the shoulders, or of the interruptions between the shoulders. In this way, a kind of key-and-lock system can be obtained, in which an abutment is guided past the stops only in defined rotation positions and brought into the starting position.

The several shoulders can be distributed on one plane in the circumferential direction, i.e. perpendicularly with respect to the longitudinal axis, about the insertion stem. It is also possible to provide shoulders on different planes along the longitudinal axis, i.e. at different axial positions. Thus, the shoulders and stops inside the receiving opening can permit a locking action at different axial positions along the abutment. The shoulders are preferably provided at a proximal end of the insertion stem, and the abutment can thus be locked at the deepest point in the implant. However, the shoulders can, for example, also be arranged centrally on the insertion stem.

An insert stop in the receiving opening of the implant and a mating insert stop on the insertion stem can be provided which, upon introduction of the abutment into the implant, limit the axial insertion movement of the abutment. The contact between insert stop and mating insert stop can thus define the axial starting position for the rotation movement, starting from which the abutment is brought from the insertion rotation position to the engaged rotation position. In this axial starting position, the insertion stem is introduced preferably completely into the implant. Insert stop and mating insert stop are advantageously provided in such a way that they bear on each other even after the abutment has been rotated to the engaged position. The abutment is thus secured in both axial directions and is held fixed in this position. When the abutment has been introduced into the starting position, the insertion stem preferably bears with a base surface on a bottom surface in the receiving opening. The base surface thus forms an insert stop, and the bottom surface forms a mating insert stop.

A rotation limit for the rotary lock can also be provided between implant and abutment. For this purpose, a rotation stop in the receiving opening and a mating rotation stop on the insertion stem can be provided, which limit a rotation movement of the abutment relative to the implant. The rotation stops can be provided, for example, as ribs or edges on the circumferential surfaces of implant and abutment and extend substantially in the axial direction. As soon as the abutment has been introduced axially into the starting position, the rotation movement takes place until the mating rotation stop bears on the rotation stop and blocks further rotation. The rotation stops are preferably positioned in such a way that the rotation movement is already blocked after a rotation of under 120°, preferably under 60°, in particular under 45°. In principle, however, a half turn or an almost full turn can be provided.

The axial stops, in the form of shoulders on the insertion stem and stops in the receiving opening of the implant, and the rotational stops, in the form of rotation stop and mating rotation stop, together produce an axial and rotational form-fit lock of the abutment in the implant. The locking position determines a predefined orientation of the abutment relative to the implant, such that a superstructure to be mounted on the abutment can likewise be provided in a pre-defined orientation.

According to the present invention, at least one shoulder of the insertion stem and at least one stop in the receiving opening are configured in such a way that abutment and implant are connected to each other by a kind of bayonet connection.

If the engagement surfaces of the shoulders are designed slightly obliquely in relation to a plane orthogonal to the longitudinal axis, as has been mentioned above, a force-fit connection between abutment and implant can also be obtained. During rotation, the shoulders are then guided along the oblique engagement surfaces and can be brought into a kind of press fit.

The shoulders on the insertion stem can be formed by depressions in a jacket surface or by projections, for example ribs, protruding radially from the jacket surface, or by a combination of both. The insertion stem can have a jacket surface with a non-circular circumferential shape, which fits into a correspondingly non-circular inner circumferential shape of the receiving opening of the implant, wherein some play remains between abutment and implant in the direction of rotation. In principle, the insertion stem can also have a non-circular circumferential shape only in the circumferential area of the shoulders. The jacket surface and inner circumferential shape can be polygonal for example, such that there are one or more rotation positions in which the abutment can be inserted into the implant. The areas of the circumferential surfaces with smaller radius can then serve as rotation stops between abutment and implant, such that abutment and implant can be rotated with said play only within the circumferential sectors of greater radius. The shoulders can be provided by depressions, for example in the form of indentations or concavities in the jacket surface, such that the shoulders do not substantially protrude radially beyond the jacket surface. The stops can be formed by projections in the inner circumferential shape of the receiving opening, which projections protrude substantially radially from the circumferential surface. The space between the jacket surface of the abutment and the inner circumferential surface of the implant can serve as a drainage channel between abutment and implant for removal of excess adhesive.

Moreover, guide surfaces or guide grooves can be provided which extend in the axial direction on the inner circumference of the receiving opening and between which the abutment or the shoulders are axially guided during insertion into the implant, and a rotation movement during said insertion is at least substantially avoided. The guide surfaces can, for example, protrude radially inward. Or the guide surfaces are formed by a non-circular inner circumferential surface of the receiving opening, as has been mentioned above. The guide surfaces for the abutment shoulders preferably end at the stops of the receiving opening, such that the insertion stem can be rotated as soon as the stops have been passed. The axial guide surfaces or grooves can merge into further guide surfaces or grooves which are oriented in the circumferential direction and lead to the stops of the receiving opening. The stops can also form such a circumferential surface. During the insertion of the abutment into the implant, the insertion stem can be axially guided with a form fit along the guide surfaces in the implant, until the axial starting position is reached in which the abutment can be rotated. The abutment is forcibly guided along the guide surfaces and guided into the pre-defined orientation with respect to the implant.

The insertion stem and the receiving opening are designed simply with a cylindrical shape. In principle, however, they can also have a conical shape.

In contrast to a screw connection between implant and abutment or to the abutment being pressed in axially, a denture system according to the present invention permits a continuous linear insertion movement. With a short rotation movement, the abutment can be brought to a desired and pre-defined position, which can be maintained without permanently applying a force. Rapid and simple handling, without repeated rotation movements, permits easy insertion and positioning of the abutment in the implant.

In the denture system illustrated, an abutment has been described which is suitable, for example, for receiving a crown. In principle, however, the implant is also suitable for receiving an abutment in the form of a gingiva shaper, an impression piece or a temporary restoration.

BRIEF DESCRIPTION OF THE FIGURES

A preferred embodiment of the invention is set forth below with reference to the figures, which serve only for explanatory purposes and are not to be interpreted as limiting the invention. Features of the invention that appear from the figures are to be understood as belonging individually and in each combination to the disclosure of the invention. In the figures:

FIG. 1 shows a three-dimensional view of a denture system according to the invention with an implant and an abutment, FIG. 2a shows a view of the denture system with an abutment in a first rotation position relative to the implant, FIG. 2b shows a detail of an insertion stem of the denture system from FIG. 2a, FIG. 2c shows a view of the denture system with the abutment in a second rotation position, FIG. 3 shows a longitudinal section through an implant of the denture system, FIG. 4 shows a longitudinal section through a denture system in which the abutment is inserted into the implant.

DETAILED DESCRIPTION

Figure 5A:
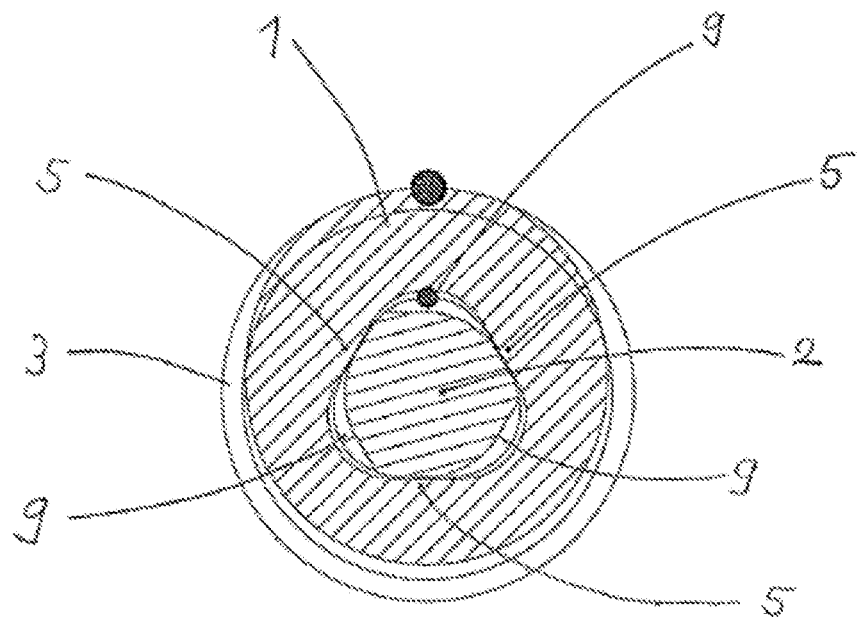
FIG. 5a shows a cross section through a denture system with an abutment in a first rotation position relative to the implant.

A denture system with an implant 1 and an abutment 2 is shown in FIG. 1. The implant 1 has a substantially cylindrical shape and runs slightly conically in the proximal area. On the outer circumference of the implant 1, an outer thread 3 is shown with which the implant can be screwed into a jawbone. Other methods of fastening in the jaw are conceivable in principle, such as are known from the prior art. At the distal end, the implant 1 has a receiving opening 4, as can be seen in FIG. 3. The receiving opening 4 extends axially and concentrically with respect to the longitudinal axis of the implant 1.

A shoulder protruding inward from the inner circumferential surface of the receiving opening 4 is interrupted in the circumferential direction in some areas, so as to form three radially inwardly protruding stops 5, of which only one is visible on the left-hand side in FIG. 3 on account of the sectional representation. The stops 5 are distributed in a substantially symmetrical manner about the longitudinal axis. Inside the implant 1, the receiving opening 4 ends with a bottom surface 16, which can have a depression at its center. Between the shoulder with the stops 5 and the bottom surface 16, a widened area 18 is formed that has a greater radius than the area with the stops 5.

The abutment 2 has an insertion stem 6 and a support 7 for a crown or the like. Insertion stem 6 and support 7 extend along a common longitudinal axis, but they could also be arranged at an angle to each other. The support 7 has an approximately cylindrical configuration and is flattened on one side, wherein the flattened part 8 serves for the orientation of the crown on the support 7. The insertion stem 6 comprises a thick distal area of quite large diameter and a thin proximal area of small diameter, at the end of which three shoulders 9 are arranged. The shoulders 9 protrude radially from the proximal area, without jutting out beyond the distal area, and they lie on a common plane extending substantially perpendicularly with respect to the longitudinal axis of the insertion stem 6. The shoulders 9 are oriented substantially point-symmetrically about the longitudinal axis of the insertion stem in trigonal form. Between the shoulders 9, interruptions or recesses 10 are provided at which the radius of the insertion stem is smaller than at the shoulders. The shoulders form a kind of trigonal end-face at the end of the insertion stem, with shoulder areas of greater radius and recess areas of smaller radius. The shoulders are thus formed as a 3-edge shoulder on the insertion stem. The end-face forms a base surface 17, which can lie in the implant 1. The distal area can have, on the outer circumference, a helical groove 11, which forms a channel running from the proximal area in the direction of the support 7. Between support 7 and insertion stem 6, a skirt 12 can be formed, which has a larger diameter than the distal area of the insertion stem 6. The skirt thus protrudes radially beyond the insertion stem 6 and, in the inserted state, can abut against a distal edge 13 of the implant 1.

In the example shown, the insertion stem 6 has three shoulders 9. In principle, however, a smaller or greater number of shoulders could be provided.

As can be seen from the detail view of the insertion stem 6 as shown in FIG. 2b, the circumferential jacket surface of the proximal area of the insertion stem is also not circular, and instead it has a likewise trigonal form. Here, flat sections 14 alternate with angled sections 15. A flat section 14 merges in each case into a shoulder 9, and an angled section 15 merges in each case into a recess 10. The angled sections 15 are offset toward the center of the recess 10. The stops 5 on the inner circumference of the receiving opening 4 likewise have a trigonal orientation. The radii or the diameters of the angled sections 15, of the shoulders 9 and of the stops 5 are matched to one another in such a way that the shoulders 9 are guided through between the stops 5 and the angled sections 15 come to lie between the stops 5 when the abutment 2 is inserted axially into the implant 1. The angled sections 15, the shoulders 9 and the stops 5 are distributed in the circumferential direction in such a way that a slight rotational play remains between the angled sections 15 and the stops 5 when the abutment 2 is introduced into the implant 1, as will be explained in more detail below.

FIGS. 2a and 2c show views of the abutment 2 in different rotation positions. In FIG. 2a, the insertion stem 6 is shown with a shoulder 9, which can be seen on the right-hand side in the figure, while an angled section 15 of the distal area lies almost at the center. In FIG. 2c, the abutment 2 has been turned through ca. 30°, such that the angled section 15 comes to lie on the left-hand side and the shoulder lies more or less at the center.

In FIG. 4, the abutment 2 is introduced axially, in an insertion rotation position, into the implant 1 and is shown in a starting position before being rotated. In the starting position, the abutment 2 is pushed axially into the implant 1 until the base surface 17 of the insertion stem 6 abuts against the bottom surface 16 of the implant 1. Moreover, the skirt 12 bears on the upper edge 13. The bottom surface 16 and the edge 13 form an insert stop, and the base surface 17 and the skirt 12 form a mating insert stop, which stops limit the insertion movement in the inserted position. Therefore, the abutment 2 cannot be pushed any further in the axial direction of insertion into the implant 2. To insert the abutment, the insertion stem 6 is oriented relative to the receiving opening 4 in a first rotation position in such a way that the recesses 10 lie opposite the stops 5 and the shoulders 9 are able to slide past between the stops. In the example shown, three different rotation positions of this kind are possible. A marking or indexing can be provided on outer areas of implant 1 and abutment 2 so as to be visible from the outside, such that the parts can be oriented relative to each other.

In FIG. 5a, implant 1 and abutment 2 are shown in cross section in the insertion rotation position. It will be seen from this how shoulders 9 come to lie between the stops 5, such that the abutment can be moved axially inside the implant.

During the insertion of the abutment 2 into the implant 1, the edges of the shoulders 9 slide through between the stops 5 and in doing so can slide along an axially extending surface of the stops. The axial surfaces, which protrude slightly radially inward, can serve as a guide surface during insertion of the abutment 2. In the starting position, the shoulders 9 come to lie axially behind the stops 5, in the widened area 18 of the receiving opening 4. The proximal area of the insertion stem 6 with the flat sections 14 and the angled sections 15 comes to lie in the area of the stops 5 and between these.

Figure 5B:
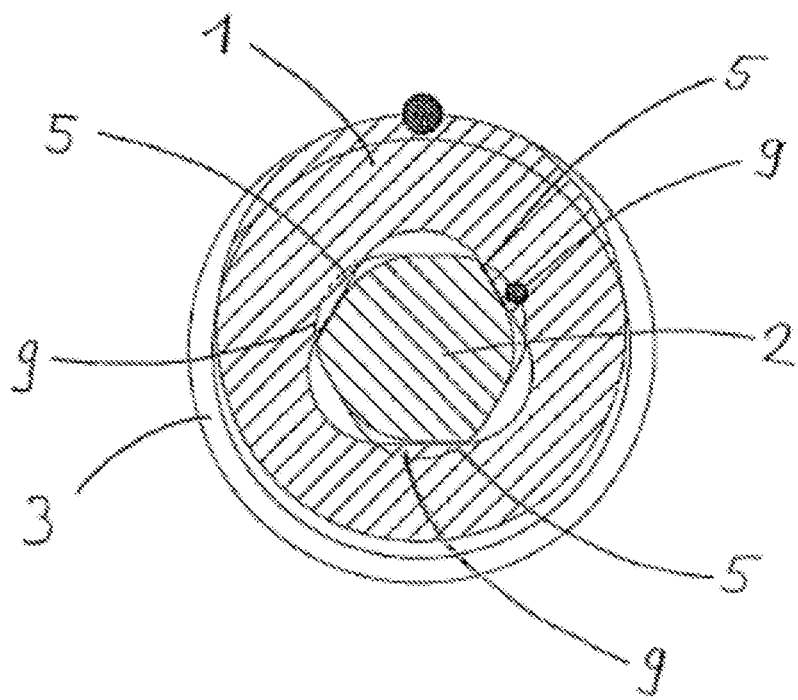
FIG. 5b shows a cross section through a denture system with the abutment in a second rotation position.

From the starting position, the abutment 2 can be rotated relative to the implant 1 about the longitudinal axis of the insertion stem 6, as described for FIGS. 2a and 2c. The shoulders 9 inside the widened area 18 are rotated to a position below or axially behind the stops 5 protruding into the receiving opening 4, such that the abutment 2 is axially locked inside the implant 1, as can be seen from FIG. 5b. In this locked rotation position, the abutment 2 with its shoulders 9 and its base surface 17 is received with a form fit between the stops 5 and the bottom surface 16.

The angled surfaces 15 can protrude radially between the stops 5 to such an extent that, during a rotation movement, they abut against the guide surfaces of the stops in the rotation direction and limit this. The radially protruding part of the angled surfaces 15 is so narrow that, between the stops 5 and the angled surfaces 15, a rotational play remains by which the insertion stem 6 inside the receiving opening 4 can be rotated through a rotation angle to the locked position. The space 19 remaining free between the stops 5 and the angled surfaces 15 is provided as a drainage channel for an adhesive. From the drainage channel, the adhesive can be carried off further through the helical channel 11 in the distal area of the insertion stem 6.

According to preferred embodiments, the distal area of the insertion stem 6 has a substantially cylindrical shape and is matched with an exact fit to the likewise cylindrical receiving opening, such that a large part of the force introduced into the abutment (for example during chewing) can be introduced from the cylindrical close fit into the implant. According to particularly preferred embodiments, the helical channel 11 is worked into the cylindrical area of the insertion stem in such a way that the close fit is not impaired, i.e. it does not protrude radially outward beyond the cylindrical jacket surface.

According to the present invention, when inserting an abutment 2 into the implant 1, all that is needed is an axial insertion movement and a small rotation movement about a short rotation angle in order to place the abutment in a predetermined position and lock it. During the insertion, adhesive located between abutment and implant is displaced and exerts a force counter to the movement of insertion of the abutment. After the abutment has been rotated to the locked position, this counter-force can be taken up by the stops 5 on the implant, while excess adhesive can be carried off through the drainage arrangement. The resulting pressure, which seeks to press the abutment out of the implant, is therefore taken up by the axial form-fit lock. The abutment can thus be fitted exactly in the implant in a simple way that does not cause problems for a patient.

LIST OF REFERENCE SIGNS 1 implant
2 abutment
3 outer thread
4 receiving opening
5 stop
6 insertion stem
7 support
8 flattened part
9 shoulder
10 recess
11 helical groove
12 skirt
13 edge
14 flat section
15 angled section
16 bottom surface
17 base surface
18 widened area
19 space

The invention claimed is:

1. A denture system comprising:
an implant for osseointegration into a jawbone, wherein the implant comprises a receiving opening,
an abutment comprising an insertion stem that can be inserted into the receiving opening,
at least one shoulder formed at a proximal end of the insertion stem, said at least one shoulder extending at least in part radially with respect to a longitudinal axis of the insertion stem, and extending partially around an outer circumferential surface of the insertion stem,
at least one stop provided in a lower region on an inner circumferential surface of the receiving opening, said stop extending radially outwards from the inner circumferential surface and partially around the inner circumferential surface, and
a widened area provided on the inner circumferential surface of the receiving opening between the at least one stop and a base surface of the receiving opening, wherein the at least one shoulder is received in the widened area when the insertion stem is inserted in the receiving opening,
wherein, in a first rotation position between the insertion stem and the implant, the abutment is movable relative to the implant in an axial direction, and, in a second rotation position, in which the insertion stem is rotated about the longitudinal axis relative to the implant by an angle with respect to the first rotation position, the at least one shoulder engages axially behind the at least one stop, whereby the abutment is fixed in the implant in the axial direction; wherein said at least one shoulder has an interruption in at least one circumferential area.

2. The denture system of claim 1, wherein said at least one shoulder comprises several shoulders formed along a circumferential direction of the insertion stem and protrude substantially radially form the insertion stem in different directions.

3. The denture system of claim 1, wherein said at least one shoulder comprises several shoulders distributed in a circumferential direction about the insertion stem on one plane.

4. The denture system of claim 1, wherein said at least one shoulder comprises several shoulders arranged symmetrically with respect to the longitudinal axis of the insertion stem.

5. The denture system of claim 1, wherein, in the second rotation position, the at least one shoulder and the at least one stop together produce a form-fit axial lock between the insertion stem and the implant.

6. The denture system of claim 1, wherein said at least one shoulder comprises several shoulders formed as an N-edge shoulder on the insertion stem, wherein N designates a number of said several shoulders.

7. The denture system of claim 1, further comprising an insert stop in or on the receiving opening and a mating insert stop on the insertion stem which, upon insertion of the abutment into the implant, limit the axial insertion movement of the abutment.

8. The denture system of claim 1, wherein, with the abutment inserted in the implant, a base surface of the insertion stem bears on a bottom surface of the receiving opening.

9. The denture system of claim 1, further comprising at least one rotation stop in the receiving opening and at least one mating rotation stop on the insertion stem, which limit a rotation movement of the abutment relative to the implant.

10. The denture system of claim 1, wherein the at least one shoulder is formed by a depression in a jacket surface of the insertion stem and/or by a rib protruding radially from the jacket surface.

11. The denture system of claim 1, further comprising guide surfaces or guide grooves which extend in the axial direction on the inner circumference of the receiving opening and between which shoulders are axially guided.

12. The denture system of claim 1, wherein the insertion stem has a jacket surface with a non-circular circumferential shape which fits into a corresponding non-circular inner circumferential shape of the receiving opening, wherein play remains in the direction of rotation between the abutment and the implant.

13. The denture system of claim 1, wherein the at least one shoulder of the insertion stem forms a bayonet connection with at least one stop in the receiving opening.

14. The denture system of claim 1, wherein the abutment is in the form of a gingiva shaper, an impression piece or a temporary restoration.

* * * * *